United States Patent
Jaiswal

(10) Patent No.: US 10,519,495 B2
(45) Date of Patent: Dec. 31, 2019

(54) EXTREME ULTRAVIOLET RADIATION IN GENOMIC SEQUENCING AND OTHER APPLICATIONS

(71) Applicant: Supriya Jaiswal, San Diego, CA (US)

(72) Inventor: Supriya Jaiswal, San Diego, CA (US)

(73) Assignee: Supriya Jaiswal, San Diego, CA (US)

( * ) Notice: Subject to any disclaimer, the term of this patent is extended or adjusted under 35 U.S.C. 154(b) by 0 days.

(21) Appl. No.: 15/422,436

(22) Filed: Feb. 1, 2017

(65) Prior Publication Data

US 2017/0218440 A1    Aug. 3, 2017

Related U.S. Application Data

(60) Provisional application No. 62/289,897, filed on Feb. 1, 2016.

(51) Int. Cl.
*C12Q 1/6869* (2018.01)
*C12N 15/10* (2006.01)
(Continued)

(52) U.S. Cl.
CPC ......... *C12Q 1/6869* (2013.01); *C12N 15/102* (2013.01); *G01N 21/33* (2013.01);
(Continued)

(58) Field of Classification Search
CPC ............... G01N 21/3103; G01N 21/33; G01N 2021/3114; G01N 2021/335; G01N 2201/0633; G01N 2201/0636–0637; G01N 23/04; G01N 23/06; G01N 23/063; G01N 23/08; G01N 23/083; G01N 23/087; G01N 2223/101; G01N 2223/1016; G01N 2223/612; C12Q 1/68; C12Q 1/6869;
(Continued)

(56) References Cited

U.S. PATENT DOCUMENTS 5,107,526 A * 4/1992 Hoover ............... G21K 7/00
378/210
6,318,869 B1   11/2001 Hudyma
(Continued)

FOREIGN PATENT DOCUMENTS

EP          0802406 A2    10/1997
JP       2012021951 A *   2/2012
WO    WO 2014/062419 A1   4/2014

OTHER PUBLICATIONS

Ekeberg, et. al., Three-Dimensional Reconstruction of the Giant Mimivirus Particle with an X-Ray Free-Electron Laser, Physical Review Letters, 114(9), 098102 (Mar. 6, 2015).*
(Continued)

*Primary Examiner* — Stephone B Allen
*Assistant Examiner* — Adam W Booher
(74) *Attorney, Agent, or Firm* — Squire Patton Boggs (US) LLP

(57) ABSTRACT

Methods, apparatus, and processes which use Extreme ultraviolet radiation (EUV) and/or soft X-ray wavelengths to read, image, edit, locate, identify, map, alter, delete, repair and sequence genes are described. An EUV scanning tool which allows high throughput genomic scanning of DNA, RNA and protein sequences is also described. A database which records characteristic absorption spectra of gene sequences is also described.

23 Claims, 2 Drawing Sheets

(51) Int. Cl.
  *G01N 21/59* (2006.01)
  *G01N 33/68* (2006.01)
  *G01N 21/33* (2006.01)
  *G01N 23/083* (2018.01)
  *H05G 2/00* (2006.01)

(52) U.S. Cl.
  CPC ......... *G01N 21/59* (2013.01); *G01N 33/6818* (2013.01); *G01N 33/6893* (2013.01); *G01N 23/083* (2013.01); *G01N 2021/335* (2013.01); *G01N 2223/612* (2013.01); *H05G 2/001* (2013.01)

(58) Field of Classification Search
  CPC ........... C12Q 2565/601; G02B 17/0647–0663; G02B 21/0004; G02B 21/16
  USPC .................... 378/51, 53, 62, 69; 250/370.09, 250/372–373; 702/20, 28; 382/129; 356/51, 326, 328, 330, 432; 359/350, 359/355, 359–360, 365–366, 368, 359/858–859
  See application file for complete search history.

(56) References Cited

U.S. PATENT DOCUMENTS

| | | |
|---|---|---|
| 9,322,964 B2 | 4/2016 | Jaiswal |
| 2005/0211910 A1 | 9/2005 | Bloom et al. |
| 2009/0227475 A1* | 9/2009 | Reverchon ............. G01N 21/33 506/39 |
| 2016/0327854 A1 | 11/2016 | Chang et al. |
| 2016/0329119 A1* | 11/2016 | Cao ........................ G21K 7/00 |
| 2017/0003419 A1 | 1/2017 | Jaiswal |

OTHER PUBLICATIONS

Ito et al., "X-ray contact microscopy system for spectromicroscopy of biological specimens", *J. Synchrotron Radiat.*, (May 1, 1998), vol. 5, No. 3, pp. 1099-1101.
International Search Report and Written Opinion dated Jun. 19, 2017 for PCT/US2017/16095 filed on Feb. 1, 2017, 16 pages.
Hua et al., "Systematic study of soft X-ray spectra of poly(Dg).poly(Dc) and poly(Da).poly(Dt) DNA duplexes", *J. Phys. Chem. B*, 2010, vol. 114, pp. 7016-7021.
Invitation to Pay Additional Fees and, Where Applicable, Protest Fee dated Apr. 10, 2017 for PCT/US2017/016095 filed on Feb. 1, 2017, 3 pages.
Van Schoot et al., "High-numerical aperture extreme ultraviolet scanner for 8-nm lithography and beyond", J. Micro/Nanolith. MEMS MOEMS, Oct.-Dec. 2017, vol. 16(4), pp. 041010-1 to 041010-16.
Ade H et al., "Chemical Contrast in X-Ray Microscopy and Spatially Resolved Xanes Spectroscopy of Organic Specimens", Science AAAS, vol. 258, Nov. 6, 1992 pp. 972-975, DOI: 110.1126/Science.1439809.
Crosetto, "Spatially Resolved Transcriptomics and Beyond", Nature Review Genetics, Jan. 1, 2015, pp. 57-66, DOI: 10.1038/nrg3832.
Extended European Search Report dated Aug. 12, 2019, for European Application EP 17748097.7, 10 pages.
Weije Hua et al., "Systematic Study of Soft X-ray Spectra of Poly(Dg)? Poly (Dc) and Poly (Da)? Poly (Dt) DNA Duplexes", Journal of Physical Chemistry Part B, vol. 114, No. 20, May 27, 2010, pp. 7016-7021, DPI: 10.1021/jp8911199e.

* cited by examiner

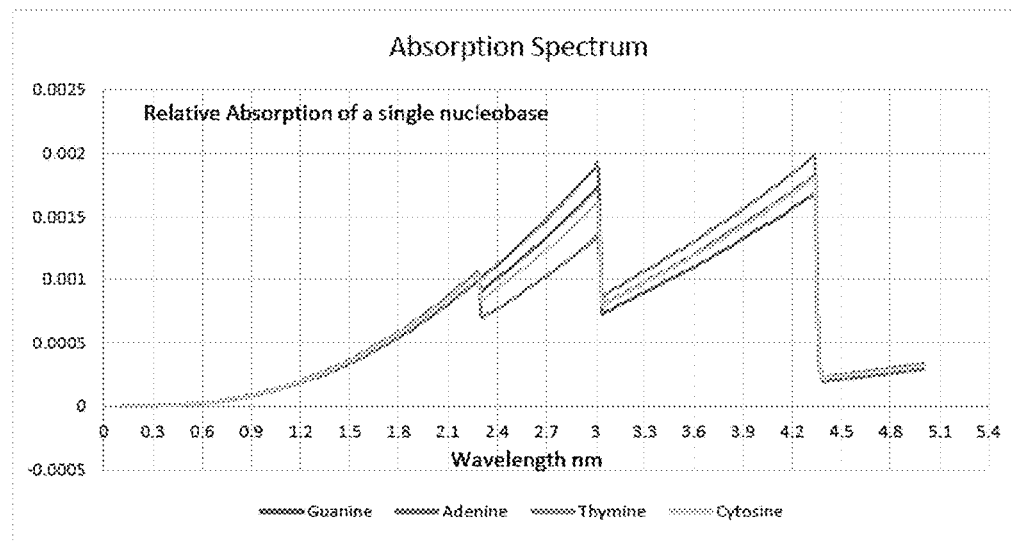
Figure 1. EUV Absorption Spectra of 4 DNA Nucleobases CGAT at normal incidence.
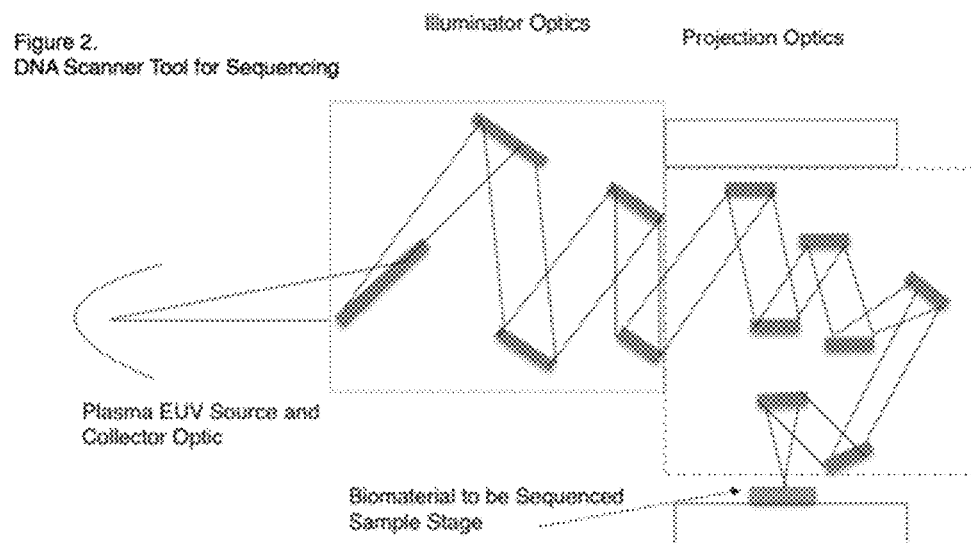

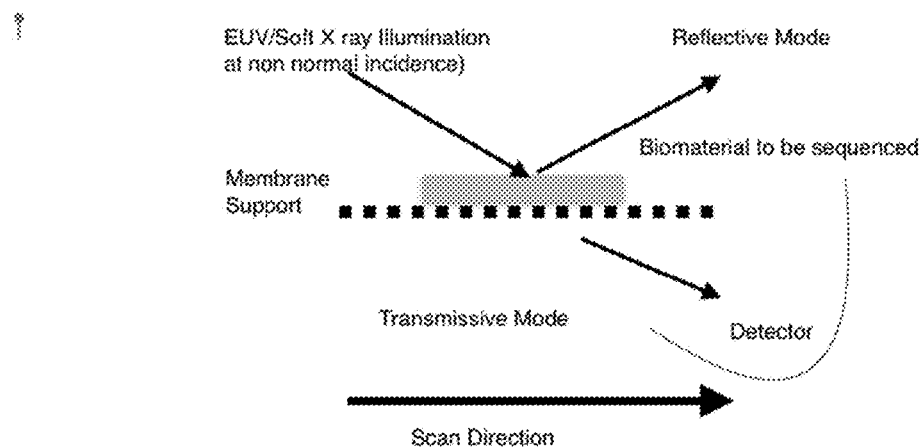
Figure 3. Reflective and Transmissive modes of identification of macromolecules
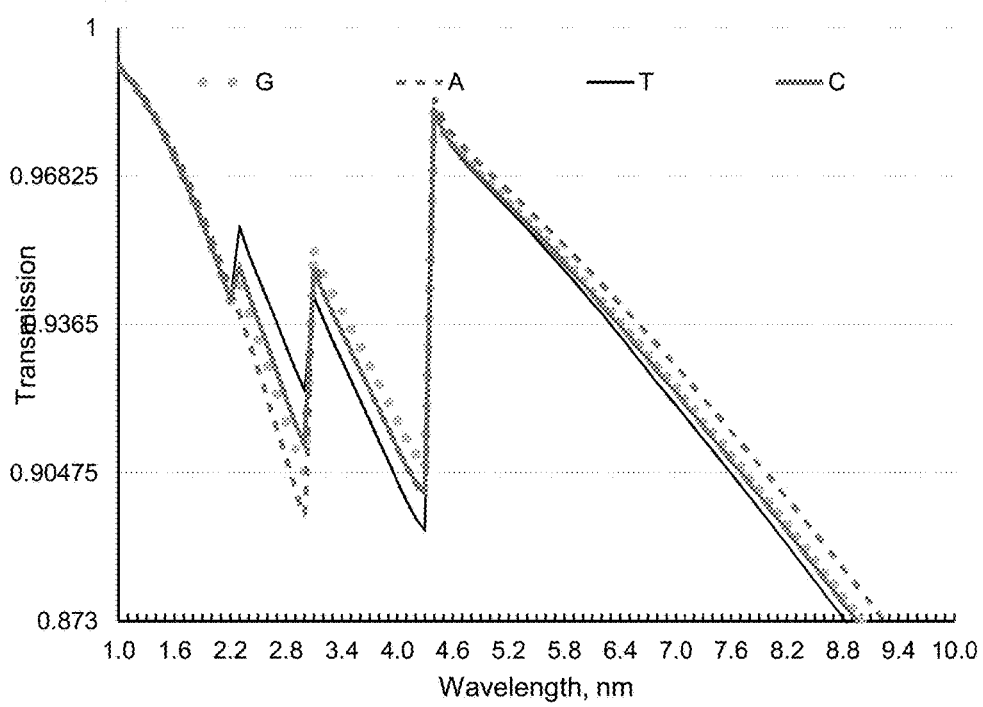
Figure 4. Transmission spectra a non normal incidence of a single nucleobase of CGAT.

EXTREME ULTRAVIOLET RADIATION IN GENOMIC SEQUENCING AND OTHER APPLICATIONS

CROSS REFERENCE TO RELATED APPLICATIONS

This application claims the benefit of U.S. Provisional Patent Application No. 62/289,897, filed Feb. 1, 2016, the content of which is incorporated herein by reference in its entirety.

BACKGROUND

Sequencing technologies such as Next Generation Sequencing (NGS) and Sanger Sequencing are used to read and identify sequence genes and base pairs of a genome. Since there are approximately 3.2 billion base pairs in the human genome a high throughput sequencing machine is needed to identify and sequence on a large scale. Next Generation Sequencing includes techniques like sequencing by synthesis using fluorescent labeled terminators and massive parallelization to provide accurate identification of genetic structure and variations. Techniques like CRISPR are used to edit gene sequences. Specific enzymes are used to target a given sequence within a set of gene sequences and repeatedly remove the identified sequence. This is the state of the art.

The aforementioned techniques have inherent advantages and disadvantages. NGS sequencing requires a high level of piecewise segmenting, massively reproducing in parallel, reassembling and referencing the gene sequence. CRISPR requires specific target primers which edit at least 20 pairs around the gene sequence of interest. So far, none of these technologies read and edit dynamically, nor allow selection of base pairs within a given gene sequence to be read and edited.

Optical lithography systems are commonly used for fabricating, for example integrated circuits and devices at having physical features at 14 nm and smaller. The resolving power of such systems is proportional to the exposure wavelength. Shorter wavelengths can improve resolution in fabrication. Extreme ultraviolet lithography (EUVL) uses electromagnetic radiation at extreme ultraviolet (EUV) wavelengths (approximately 124 nanometers to 0.1 nanometers). Accordingly, photons at these wavelengths have energies in the range of approximately 10 electron volts (eV) to 12.4 keV (corresponding to 124 nm and 0.1 nm, respectively). Using EUV wavelengths for lithography has potential advantages of reducing feature sizes in devices to less than 10 nm or more such as semiconductor chips as well as in other applications such as polymer electronics, solar cells, biotech, and medical technologies.

So far none of these technologies can read and edit at the same time, nor allow random selection of base pairs within a given gene sequence to be dynamically read and edited.

SUMMARY

In one aspect, this disclosure relates generally to the use of Extreme Ultraviolet (EUV) radiation, soft X-ray radiation in a biotech application to selectively locate, read, identify a gene or gene sequence either inside or outside a biological cell. It further relates to dynamically and/or randomly and/or selectively editing, deleting, altering and/or repairing a gene at a given location within a genomic sequence. Provided herein is a method to sequence selectively and non-sequentially without the need for DNA synthesis, biomolecule tagging, fluorescent labeling, DNA replication, enzyme cleaving, parallelization, depth of coverage, alignment to a reference genome, nano pore channels, shot-gun sequencing, ion detection, or nucleotide addition, all of which introduce complexity, inaccuracy and time in sequencing.

In another aspect, this disclosure also relates to the design of a next generation EUV high throughput tool or apparatus to machine read and alter gene sequences in real time. The architecture of the tool or apparatus comprises a set of one or more illuminator optics, projection lenses or mirrors, light focusing device, EUV or soft x ray light source, a collector optic, sample stage. The tool may be used in scanning mode to 2D or 3D scan DNA sequences. Extreme ultraviolet wavelengths may be generated artificially by devices such as plasma and synchrotron light sources or solid targets, or a liquid droplet source. In one embodiment, provided are six or more high numerical aperture projection mirrors, four or more illuminator mirrors, one collector and a sample stage. The mirrors may be parabolic, aspherical or freeform. In certain embodiments, at least 6 projection mirrors are useful to achieve sufficient spatial resolution for single digit resolution nucleobase sequencing. A higher power light source is also desirable to increase the scanning throughput or number of base pairs sequenced per hour.

A light system or apparatus such as an EUV lithography tool can be used to focus light to sub 20 nm spot sizes. Extreme ultraviolet lithography (EUVL) uses electromagnetic radiation at extreme ultraviolet (EUV) wavelengths (approximately 124 nanometers to 0.1 nanometers). Accordingly, photons at these wavelengths have energies in the range of approximately 10 electron volts (eV) to 12.4 keV (corresponding to 124 nm and 0.1 nm, respectively). Extreme ultraviolet wavelengths may be generated artificially by devices such as plasma and synchrotron light sources or solid targets. When this light is incident on a gene sequence a proportion of the light will be absorbed. Each base or base pair of the gene sequence will generate a characteristic absorption spectrum at a discrete EUV frequency. If such a spectrum is detected or decomposed from a cumulative absorption spectra set, then this can help identify the specific base pair. The smaller the wavelength used the smaller the focused spot size, and the higher the imaging resolution. For a wavelength of light of 2.8 nm and a Numerical Aperture (NA) of 0.5 the spot size will be 2.8 nm approximately. For example a single nucleobase has a length of 0.34 nm. This means that the imaging resolution is 9 bases (2.8/0.34). With projection mirrors the limit of resolution can be decreased further. This is governed by the formula k1*wavelength/NA, where k1 is a constant factor which determines the resolution limit that can be achieved by the lithography tool. Assuming a k1 factor of approximately 0.25, the limiting resolution (k1*wavelength/NA) is 1.4 nm or 4-5 bases. Using a magnification factor of 4× or 8× the resolution limit may be smaller, up to 1-2 base pairs. Since the spectra has resonance peaks at discrete frequencies, it is possible to decompose further, use base pairing information and differences between absorption spectra from two overlapping adjacent sets, cumulative absorption at measured at three spectral peaks to get more resolution sequencing. Gene identification should be possible from the measurement of the cumulative spectra and phase information. It is expected that light of wavelength 13.5 nm and smaller, specifically 2-4 nm range, (including 4.3 nm and 2.8 nm) will be suitable for these applications. Absorption spectra may equally be exchanged for transmission spectra or reflection spectra in this disclosure. Detectors can measure a sensitivity difference in absorption signal as small as $1\times10^{-4}$. This makes it possible to distinguish cumulative differences of one nucleobase.

In an embodiment the process of reading, scanning or imaging a gene sequence or nucleobase includes the process of measuring its unique absorption spectra and identifying the gene from a known or simulated spectrum.

In another aspect of this disclosure, a gene sequence or set of nucleobases may also be edited, altered, repaired or deleted at a given location or address. The deletion occurs by focusing the light spot on the desired sequence at a given location and increasing the intensity of the light or the power delivered to the focused spot to sever the link between two base pairs through photo-absorption, or sever the base, and preventing regeneration. In certain embodiments the action of editing or deleting a subset of a sequence may occur consecutively to reading the sequence. Depending on the spot size and intensity of the light one or more gene sets can be deleted at any given location. More than one focused spot may also be used to achieve multiple simultaneous solutions.

In a typical embodiment gene sequences include sub elements like DNA and RNA nucleobase pairs, Cytosine, Guanine, Adenine, Thymine, Uracil. Gene sequences in this disclosure also include biomaterials like DNA and RNA strands, reads, single nucleotide polymorphisms (SNPs), bases, proteins, primers, amino acid sequences, oligonucleotides, peptides, copy number variants, mutations, variants, enzymes, exomes, molecules, nucleotides, alleles, chromosomes, telomeres, without limitation to the species. Each of the five possible bases, Guanine, Cytosine, Adenine, Thymine and Uracil, has a different chemical structure which is a combination of Carbon, Hydrogen, Oxygen and Nitrogen with different relative ratios of each element. Since EUV/Soft-Xray absorption is sensitive to presence of theses elements, each base will have a distinct and unique signature absorption spectrum at EUV wavelengths. In examples were the absorption spectra of one or more bases are obtained at once, the absorption spectra can be decomposed into the individual base spectrums as described above. A database or library of identifiable gene sequences, nucleobases, proteins, RNA and DNA containing their respective absorption spectra signatures is generated.

This disclosure improves over the existing state of the art next generation sequencing (NGS) technologies because it allows for simultaneous or dynamic reading, or imaging, mapping, and editing or deleting of gene sequences in a given genome on a per individual basis. Current gene sequencing technologies such as whole genome shotgun sequencing, de novo sequencing or Sanger sequencing only allow for sequencing genes, after destruction, replication and referencing to the standard reference genome. In this disclosure, a genomic map which can also be described as a gene ontology network or a gene sequence map is generated. The entire sequence is recorded sequentially at least one time by measuring the absorption and phase spectrum of each nucleobase, or each gene at each possible location. The physical coordinates of each nucleobase, or set of nucleobases, are registered as an address, together with other global and local identifiers and landmarks. Each gene, its absorption spectrum and gene position are recorded in this way. Subsequently, should a specific gene sequence once identified need to be selectively or dynamically targeted, relocated or deleted, it can be done by using the respective registration address to reposition the focus of the light source spot for delivering intense radiation. EUV radiation has sufficient spatial and spectral resolution to physically and spectrally discriminate different gene sequences and spatial control for selectively targeting specific gene sequences. In NGS technologies there is no possibility of dynamically returning to a specific location in the sequence or editing the sequence in real time while being read.

This disclosure improves over the existing state of art editing technologies such as CRISPR interference technique (clustered regularly-interspaced short palindromic repeats), which rely on specific enzyme sequences to cleave the sequence or cut the genome at a specific target location which matches the enzyme sequence. The limitations of CRISPR are that only one type of target sequence can be deleted at any one time, and all instances of that target sequence in all locations, if repeated in the genome, are cut. Additionally, the sequence tries to repair itself after being cut repeatedly. Not only is the sequence cut, but a region of up to 20 base pairs around the target location is also cut. In EUV radiation sequencing and deletion multiple random targets with differently specified sequences can be edited in a single instance. Similarly, single instances of a specific target can also be edited, with a spatial resolution of up to 1-2 base pairs.

In addition to sequencing this disclosure also describes the use of EUV radiation and soft Xray, methods and apparatus described herein, in the application of genotyping, i.e. the process of determining which genetic variants an individual possesses. In an embodiment EUV radiation can be used to sequence a segment of a sequence such as an exome rather than the entire genome and examine variants in SNPs and regions of commonality. The process can also be used to examine germline or somatic mutations, epigenetic variations, cancer and inheritance variations. EUV radiation sequencing can also be used for expression profiling.

The methods and apparatus described herein include the application to a variety of species including, humans, bacteria, animals, plants, yeast, mammalian cells.

A DNA, RNA or other strand may be extracted from and cell, linearized, planarized and aligned prior to sequencing in most instances. With EUV radiation sequencing a DNA segment may be additionally sequenced intracellularly and three dimensionally (3D—one or more dimensions), and nonlinearly. Typically chromatin binds the DNA strands together making intracellular sequencing challenging. With absorption sequencing as described in this disclosure, chromatin would have a different absorption spectrum to the discrete DNA spectrum with three spectral peaks and therefore could be distinguished from the DNA sequence.

When imaging a sequence intracellularly the cell may be optically trapped with two or more lasers beams use to hold the cell in position while the sequencing occurs. Another laser may also be used to cut an insertion path in the cell membrane or cell wall or through cytoplasm to reduce the absorption of EUV by other components in the cell. Other components in the cell may also be distinguished by a different spectral absorption curves.

The sequencing of genomes requires a significant amount of data analysis and bioinformatic post-processing of data. It is beneficial to use self learning and predictive algorithms (and other known information about the location of landmark genes) to decompose groups of absorption spectra to save on computational, measuring and reading time. Furthermore for larger spot sizes larger groups of nucleobases can be sequenced with less sampling resolution, and identified from known spectra such as those in a reference database or library, or previously measured samples rather than individual measurements.

BRIEF DESCRIPTION OF THE DRAWINGS

The present disclosure may be more fully appreciated in connection with the following detailed description taken in conjunction with the accompanying drawings, wherein:

FIG. 1 illustrates calculated absorption spectra for DNA nucleobases C, G, A, T at EUV wavelengths calculated according to the Examples herein.

FIG. 2 illustrates a DNA Scanner system with plasma lightsource and projection mirror system for gene sequencing.

FIG. 3 illustrates a method of detecting either reflected or absorbed radiation from a macromolecule. Light illumination as close as possible to grazing incidence is preferred due to the increased absorption.

FIG. 4 illustrates transmission spectra from G, C, A, T at non normal incidence of a single nucleobase.

DETAILED DESCRIPTION OF THE INVENTION

Provided herein are apparatuses and methods useful for locating, reading, identifying, and/or editing macromolecules.

a. Definitions

When referring to the apparatuses and methods provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "extreme ultraviolet" or "EUV" refers to electromagnetic radiation in the part of the electromagnetic spectrum spanning wavelengths from 124 nm down to 10 nm. The radiation has photons with energies from 10 eV up to 124 eV.

The term "soft X-ray" refers to electromagnetic radiation in the part of the electromagnetic spectrum spanning wavelengths from 10 nm down to 0.1 nm. The radiation has photons with energies from 0.1 eV up to 10 eV. Extreme Ultraviolet, EUV and soft X-ray are used interchangeably in this disclosure to represent the full range from 0.1 nm to 124 nm.

The term "macromolecule" refers to a high molecular weight molecule having at least 1000 Da. Useful macromolecules include polymers of repeating monomers. Examples include polynucleotides, DNA, RNA, polypeptides, proteins, peptides, viruses, and oligosaccharides.

The term "spot size" refers to the diameter of a radiation beam that is capable of interacting with a target. In embodiments where the radiation beam contacts a support, the spot size is the diameter of the radiation beam or beam waist that intersects the support. The spot may be a focused or collimated radiation beam by a lens or mirror system, to a minimum spot size defined by the Airy disc, and dependent on the wavelength of the radiation beam. In fact the radius of the minimum spot size is defined by $1.22\lambda f$, where f is the f number of the lens, the first dark circle in the Airy pattern. In lithography systems a given resolution is achieved by the overall magnification from a set of projection mirrors and the Numerical Aperture (NA) of the system. Resolution, or the minimum spot size is defined as $k1\lambda/NA$ where k1 is the resolution factor and k1 is approximately 0.25. Lithography systems today have already achieved a 4× magnification and 0.5 NA. For a 2.8 nm wavelength, this is a resolution of 0.7 nm or 2 base pairs. Higher magnification can be achieved by increasing the number of projection mirrors to focus to a smaller spot size sand larger system numerical apertures. For a 8× magnification single base pair resolution will be possible.

a. Apparatuses

Provided herein are apparatuses useful for locating, reading, identifying, and/or editing macromolecules. The apparatuses generally comprise a radiation source, one or more macromolecules configured to absorb at least a portion of the radiation, and a detector capable of detecting transmitted and/or absorbed radiation.

In certain embodiments, the radiation source is capable of transmitting radiation having a wavelength from 0.1 nm to 250 nm. In certain embodiments, the radiation source is capable of transmitting extreme ultraviolet radiation and/or soft X-ray radiation. In certain embodiments, the radiation source is capable of transmitting extreme ultraviolet radiation. In certain embodiments, the radiation source is capable of transmitting soft X-ray radiation. In certain embodiments, the radiation source is capable of transmitting radiation having a wavelength from 0.1 nm to 10 nm. In certain embodiments, the radiation source is capable of transmitting radiation having a wavelength from 1 nm to 10 nm. In certain embodiments, the radiation source is capable of transmitting radiation having a wavelength from 1 nm to 250 nm. In certain embodiments, the radiation source is capable of transmitting radiation having a wavelength from 10 nm to 250 nm. In certain embodiments, the radiation source is capable of transmitting radiation having a wavelength from 10 nm to 200 nm. In certain embodiments, the radiation source is capable of transmitting radiation having a wavelength from 10 nm to 150 nm. In certain embodiments, the radiation source is capable of transmitting radiation having a wavelength from 10 nm to 124 nm. In certain embodiments, the radiation source is capable of transmitting radiation having a wavelength from 0.1 nm to 124 nm.

The radiation source can be any radiation source deemed useful by the practitioner of skill. Useful radiation sources are commercially available. Useful examples include plasma and synchrotron light sources or solid targets. EUV light sources include high order harmonic x-ray generation sources, EUV beamline synchrotrons, EUV solid targets, and plasma based sources. E.g. nickel like tin produces EUV radiation at 11.9 nm and nickel like silver produces EUV radiation at 13.9 nm and tin droplets produce EUV radiation at 13.5 nm. Light sources may be laser driven e.g. laser produced plasma or electrically driven, e.g, electrically discharged plasma and be continuous or pulsed. Electrodeless Z-Pinch sources may also be used e.g. Energetiq EQ-10SXR in which has a wavelength range in the 2-4 nm and delivers 400 mW of power at 2.8 nm using nitrogen. Liquid jet, tin, or xenon plasmas are also used. For example a tin plasma source has a EUV range from 8 to 19 nm and a xenon plasma source has an EUV spectrum range from 8 to 19 nm with a higher intensity range from 11 to 15 nm. In solid targets electrons are used to bombard a given target and generate x rays.

The radiation source can be configured to transmit the desired radiation wavelengths using techniques known to those of skill in the art. The main way of tuning the radiation source involves mirror systems such as Molybdenum Silicon (Mo/Si) multilayers which select an in band of radiation from e.g. from 13-14 nm, by reflecting only those frequencies and absorbing other frequencies. Similarly Carbon Titanium multilayers may be used at 2.8 nm to select a band of radiation.

In the apparatuses, the radiation source is configured to transmit radiation that contacts one or more macromolecules. The macromolecules are configured to absorb at least a portion of the radiation. Those of skill will recognize that the macromolecules can also transmit a portion of the radiation.

In order to contact the macromolecule with the radiation, the apparatus can further comprise one or more focusing components capable of focusing the radiation to contact the macromolecule. The focusing components can be any component capable of focusing the radiation transmitted from the source. In certain embodiments, the focusing components are one or more mirrors. In certain embodiments, the focusing components are one or more lenses. In certain embodiments, the focusing components are one or more reflectors. In certain embodiments, the focusing components are a combination of one or more mirrors, lenses, and/or reflectors. Exemplary configurations for focusing components are provided in the Examples and FIG. 2. In certain embodiments, an apparatus comprises at least six high numerical aperture projection mirrors and at least four illuminator mirrors. The mirrors may be parabolic, aspherical or freeform. In certain embodiments, the at least 6 projection mirrors provide sufficient spatial resolution for single digit resolution nucleobase sequencing. For higher resolution more mirrors may be used, or higher numerical aperture systems which focus to a smaller spot size. 6 projection mirrors can achieve 4× magnification. Between 8-12 mirrors may be necessary for 8× magnification or single base pair resolution.

Mirrors also known as reflectors may contain multilayer coatings. Examples of multilayers in the Soft X ray region include Ti/Ni, Ca/Co, Sc/Ni, Mg/Ni, Be/Ni, B4C/Ru, C/Fe and Sc/Wc, Ba/Co, Ca/Co, C/Co. Mirrors may also be nanoscale combinations of a single base material e.g Ni or Co or Mo and may contain other nanoscale combinations of materials in two or three dimensions. Physical sizes of mirrors range from small 1-10 cm diameter up to 1 m diameter or larger depending one the size of the tool and the capture area. Mirrors consist of a substrate plus a coating and the substrate may be Silicon, Silica or Be.

In certain embodiments, the radiation spot size is 0.1-100 nm. In certain embodiments, the radiation spot size is 1-100 nm. In certain embodiments, the radiation spot size is 10-75 nm. In certain embodiments, the radiation spot size is 10-50 nm. In certain embodiments, the radiation spot size is 10-25 nm. In certain embodiments, the radiation spot size is 10-230 nm.

The apparatuses further comprise one or more macromolecules configured to absorb at least a portion of the radiation. Useful macromolecules are described in detail below. Each macromolecule can be configured to absorb the radiation using standard techniques and components. The macromolecule can be presented in the radiation in solution, or on a solid support, or in any other form deemed suitable to the person of skill. The macromolecule in solution can be presented in a cuvette, in a microtiter well, microfluidic device or channel, on a slide, or in or on any other suitable medium.

In certain embodiments, the macromolecule is provided on a solid support. The solid support can be any material suitable for supporting a macromolecule. Useful support materials include glass, ceramic, silica, polycarbonate, PDMS and silicon. Depending on whether the system is used in reflective or transmission mode, either a membrane support for transmission or a super polished or flat substrate can be used to hold the macromolecule Examples of useful solid supports include microscope or slides, silicon wafers, graphene films, imaging or registration grids. Membranes support include silicon nitride, silicon dioxide, porous films, carbon grids or holey grids. The supports can be obtained from commercial suppliers or manufactured according to standard techniques.

The supports can comprise any number of macromolecules. In certain embodiments, each support provides a single macromolecule. Advantageously, certain apparatuses and methods provided herein facilitate sequencing of a single macromolecule. In further embodiments, each support provides a plurality of macromolecules. The apparatuses and methods provided herein also facilitate sequencing of a number of macromolecules. In certain embodiments, a plurality of macromolecules can be sequenced in parallel. In certain embodiments, a plurality of macromolecules can be sequenced simultaneously.

When the support provides a plurality of macromolecules, the density of macromolecules can be any density suitable for the methods described herein. The approach seeks to identify single units of macromolecules.

In certain embodiments, the support is provided on a stage that is capable of moving the one or more macromolecules. For instance, the stage can be capable of translating the macromolecule in any direction relative to the radiation. In certain embodiments, the stage is capable of moving the macromolecule so that a first monomer of the macromolecule contacts the radiation. The first monomer can be any monomer in the macromolecule—a terminal monomer or an internal monomer. In certain embodiments, the stage is capable of moving the macromolecule so that a second monomer of the macromolecule contacts the radiation. In certain embodiments, the second monomer is adjacent to the first. In certain embodiments, the stage is capable of moving the macromolecule in discreet distances of one monomer per movement. In such embodiments, the stage is capable of moving the macromolecule through the radiation one monomer at a time. For instance, in a first position, monomers n through m of the macromolecule might contact the radiation. After movement to a second position, monomers n+1 through m+1 would contact the radiation. The distance m-n would vary and depend on the spot size of the radiation beam incident on the macromolecule.

Useful stages for the above component are known to those of skill in the art. Examples include nanopositioners, piezo stages, nanopositioning stages, encoders. These stages have translational and rotational capability, in 3 dimensions, with a resolution of 0.1 nm. Since one base has an approximate distance of 0.34 nm this is sufficient to resolve or translate across a single base.

Detection of a macromolecule constituent can be done in reflective or transmissive mode. If in reflectance mode the reflectivity spectra is recorded from the plane of the incidence angle and spectral peaks at specific wavelengths indicate the absorption. If in transmissive mode then spectral dips in the absorption spectra identify the absorption signature. This is shown in FIG. 3.

Macromolecules

The macromolecule can be any macromolecule deemed suitable by those of skill in the art. In certain embodiments, the macromolecule is a polymer. In certain embodiments, the macromolecule is a polypeptide. In certain embodiments, the macromolecule is a peptide or protein. In certain embodiments, the macromolecule is a polynucleotide. In certain embodiments, the macromolecule is DNA. In certain embodiments, the macromolecule is RNA. In certain embodiments, the macromolecule is an oligosaccharide.

The macromolecule can be prepared by any method deemed suitable by those of skill. The macromolecule can also be obtained from any source deemed suitable by those of skill. In certain embodiments, the macromolecule is synthetic. In certain embodiments, the macromolecule is of cellular origin. In certain embodiments, the macromolecule is isolated from a cell. In certain embodiments, the macromolecule is within a cell.

Generally, the macromolecule is presented on a support, as discussed above. The macromolecule can be resting on the support. In certain embodiments, the macromolecule is immobilized on the support. The macromolecule can be immobilized on the support by any technique deemed suitable. In certain embodiments, the macromolecule is linked to the support via a non-covalent interaction. Examples of non-covalent interactions include electrostatic interactions and hydrophobic interactions. In certain embodiments, the macromolecule is linked to the support via one or more covalent bonds. In certain embodiments, the support is derivatized for linking to a macromolecule. A glass support can be derivatized, for example, by silanization with amino or epoxide or mercapto groups. Macromolecules linked to amino, succinyl, or sulfur groups can be immobilized covalently on such derivatized by standard techniques. In certain embodiments, the support is derivatized with biotin and the macromolecule is linked to avidin via standard techniques. In certain embodiments, the support is derivatized with avidin and the macromolecule is linked to biotin via standard techniques. In such embodiments, the immobilization linkage is formed by the interaction of avidin and biotin.

The supported macromolecule is thus configured for contact with the radiation. In certain embodiments, the support is moved to position the macromolecule, or a portion thereof, in the radiation. The radiation source, the optional optics, and the support are configured so that the radiation contacts the macromolecule. The detector is configured to detect radiation absorbed and/or transmitted and/or re-emitted by the macromolecule.

Methods

In the methods provided herein, a radiation source generates radiation. The radiation contacts a macromolecule which absorbs at least a portion of the radiation. Radiation absorbed and/or transmitted by the macromolecule is detected by a detector.

In polynucleotide sequencing methods, each base or base pair of a polynucleotide provides a characteristic absorption spectrum at discrete EUV frequencies. Exemplary absorption spectra are provided in the Figures and Examples herein. If a single base or base pair is responsible for the absorption, that base pair can be identified from the absorption spectrum. If a plurality of bases or base pairs is responsible for the absorption, decomposition of the absorption spectrum can identify the contributing bases or base pairs. In certain embodiments, the stage is moved through the radiation spot size. Changes in the composite absorption spectrum at different wavelengths indicate which bases or base pairs moved out of the radiation spot and which bases or base pairs moved into the radiation spot. From these changes, the methods can identify the bases or base pairs that moved out of the radiation spot and the bases or base pairs that moved into the radiation spot. These identified bases or base pairs provide sequence information for the macromolecule. Accordingly, provided herein are methods for identifying the sequence of a macromolecule.

In certain embodiments, the methods provided herein are applied to a number of polynucleotides. The absorption spectra of these polynucleotides are stored along with the base or base pair sequence of the polynucleotide. In these methods, a library of spectra and corresponding sequences is developed. This library facilitates the identification of the sequences of new polynucleotides. In certain embodiments, provided herein are methods of machine-based learning of the spectra and their corresponding sequences. As the components of the present apparatuses accumulate more and more spectra and sequences, they become more proficient at identifying sequences from new spectra.

In this embodiment the process of reading, scanning or imaging a gene sequence or nucleobase includes the process of measuring its unique absorption spectra and/or identifying the gene from a known or simulated spectrum.

In another aspect of this disclosure, a gene sequence or set of nucleobases may also be edited, altered, repaired or deleted at a given location or address. The deletion occurs by focusing the light spot on the desired sequence at a given location and increasing the intensity of the light or the power delivered to the focused spot to severe the link between two base pairs through photo-absorption, or severe the base, and preventing regeneration. In certain embodiments the action of editing or deleting a subset of a sequence may occur consecutively to reading the sequence. Depending on the spot size and intensity of the light one or more gene sets can be deleted at any given location. More than one focused spot may also be used to achieve multiple simultaneous solutions.

In certain embodiments, provided herein are methods for cutting a macromolecule. In any of the configurations above, the intensity of the radiation on a macromolecule can be increased to a high intensity, sufficient to cut one or more bonds of the macromolecule. In certain embodiments, a particular sequence of the macromolecule is identified, as described above. When the sequence is identified in the apparatus, the intensity of the radiation is tuned to cut the macromolecule. Such embodiments provide sequence-specific cutting of a target sequence in a macromolecule. In these embodiments, the macromolecule can be a peptide or protein, and the macromolecule can be a polynucleotide such as DNA or RNA.

In certain embodiments a 3D map or network of the gene ontology or macromolecule may be formed. This includes a registration database of the physical and sequence location of each gene. After mapping each sequence the location of a given sequence can be dynamically addressed, and edited or repaired at a specific location.

EXAMPLES

Example 1

In a molecular spectral evaluation, each nucleobase is contacted with EUV radiation at wavelengths from 0 nm to 5.0 nm. Absorption spectra for each nucleobase is calculated and provided in FIG. 1 and transmission spectra FIG. 4. C, G, A and T have unique spectra due to their unique molecular combinations and densities. In some cases the spectral signature consists of 3 spectral dips in FIG. 4 (Guanine) at wavelengths of 2.2 nm (oxygen), 2.8 nm (nitrogen) and 4.3 nm (carbon and hydrogen) and some cases such it consists of 2 spectral dips (Adenine) at 2.8 nm and 4.3 nm wavelength. Furthermore the relative spectral intensity of each of the spectral dips is proportional to the number of oxygen (at 2.3 nm wavelength) atoms, nitrogen atoms (at 2.8 nm wavelength) and carbon atoms (at 4.3 nm wavelength) present in each nucleobase of the macromolecule. H atoms are relatively transparent. In this way organic molecules, peptides, amino acids can be identified and correlated with their known structure. Additionally, information about known pairing structure, and spatial information to help further identify the constituent of the macromolecule.

Example 2

In some cases the macromolecule has an identifier atom, e.g. a Chlorine atom. In this case an additional spectral dip is observed at another wavelength e.g at 6.5 nm Since plasma sources for EUV and Soft x ray are broad in their spectral range some macromolecule constituents with unique atoms can easily be identified.

All publications and patent, applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof.

What is claimed:

1. An apparatus for detecting absorption by a macromolecule comprising:
   i. a radiation source configured to transmit radiation having a wavelength from 0.1 nm to 250 nm;
   ii. one or more focusing components configured to focus the radiation to a spot size of less than 20 nm;
   ii. a macromolecule comprising a sequence of monomers configured to absorb at least a portion of the radiation;
   iv. a detector capable of detecting radiation absorbed by the macromolecule, where each monomer in the macromolecule has a unique signature in the absorption spectrum; and
   v. a decomposer configured to convert the absorption spectrum from the detector into an identified sequence of monomers of the macromolecule, said monomers selected from the group consisting of cytosine, guanine, adenine, thymine, and uracil.

2. The apparatus of claim 1 wherein the radiation source is an extreme ultraviolet source (EUV).

3. The apparatus of claim 1 wherein the radiation source is a soft X-ray source.

4. The apparatus of claim 1 wherein the one or more focusing components capable of focusing the radiation is present and selected from one or more mirrors, lenses, or reflectors, and combinations thereof, capable of focusing the radiation on the macromolecule.

5. The apparatus of claim 1 comprising one or more mirrors configured to focus the radiation to a spot size of less than 20 nm.

6. The apparatus of claim 1 comprising a stage configured to contact the macromolecule within the radiation.

7. The apparatus of claim 6 wherein the stage is configured to translate the macromolecule within the radiation.

8. The apparatus of claim 1 wherein the macromolecule is a genomic sequence, DNA sequence, RNA sequence, oligonucleotide, nucleotide, base pairs, single nucleotide polymorphism, mutation, copy number variant, sequence of base pairs, bacteria, allele, chromosome, or molecule.

9. The apparatus of claim 1 wherein the macromolecule is a nucleic acid.

10. The apparatus of claim 1 for locating a macromolecule sequence.

11. The apparatus of claim 1 for reading a macromolecule sequence.

12. The apparatus of claim 1 for editing a macromolecule sequence.

13. A method for genotyping comprising the steps of operating the apparatus of claim 1; obtaining a sequence of the macromolecule from the system; and identifying the genotype of the macromolecule from the sequence.

14. The identification of a gene sequence derived from using the apparatus of claim 1 using a self learning algorithm or predictive sequencing algorithm.

15. A system for locating, reading, identifying and editing one or more gene sequences, comprising:
   an EUV or soft X ray light source configured to transmit light having a wavelength in the range 0.1 nm to 250 nm,
   a mirror, lens, or reflector for focusing the light spot size,
   a biomaterial to be sequenced,
   a measured absorption spectrum or transmission spectrum; and
   a decomposer configured to convert the measured absorption or transmission spectrum into an identified sequence of monomers of the biomaterial, said monomers selected from the group consisting of cytosine, guanine, adenine, thymine, and uracil.

16. The system of claim 15, wherein the biomaterial is a genomic sequence, DNA sequence, RNA sequence, oligonucleotide, nucleotide, base pairs, single nucleotide polymorphism, mutation, copy number variant, sequence of base pairs, bacteria, allele, chromosome, or molecule.

17. The system of claim 15 that further comprises a projection lens system with at least 6 projection mirrors and a plasma light source.

18. A method for generating a genomic map comprising the steps of operating the system of claim 15; obtaining a sequence of the macromolecule from the system; and generating a genomic map from the sequence.

19. A method using the system of claim 15 comprising the steps:
   contacting the biomaterial with the light from the EUV or soft X ray light source;
   obtaining the absorption spectrum or transmission spectrum;
   obtaining the sequence of a plurality of residues of the biomaterial from the absorption spectrum or transmission spectrum.

20. The method of claim 19, wherein the biomaterial is a nucleic acid and the sequence is sequence of nucleic acid bases.

21. The method of claim 19, wherein the biomaterial is a nucleic acid and the sequence is a genomic map.

22. The system of claim 15 comprising a plurality of mirrors, and/or lenses, and/or reflectors configured to focus the light spot size to less than 20 nm.

23. The system of claim 15 comprising a plurality of projection mirrors configured to focus the light spot size to less than 20 nm.

* * * * *